United States Patent [19]

Furuhashi et al.

[11] Patent Number: 5,376,539
[45] Date of Patent: Dec. 27, 1994

[54] PROCESS FOR THE PREPARATION OF EPOXIDES BY MEANS OF MICROORGANISMS

[75] Inventors: Keizo Furuhashi; Motoyoshi Takagi, both of Saitama, Japan

[73] Assignee: Nippon Mining Co., Ltd., Tokyo, Japan

[21] Appl. No.: 956,042

[22] Filed: Oct. 2, 1992

Related U.S. Application Data

[60] Division of Ser. No. 700,326, May 9, 1991, abandoned, which is a continuation of Ser. No. 268,648, Nov. 8, 1988, abandoned, which is a continuation of Ser. No. 737,966, May 28, 1985, abandoned.

[30] Foreign Application Priority Data

| May 28, 1984 | [JP] | Japan | 59-108040 |
| Sep. 3, 1984 | [JP] | Japan | 59-184332 |
| Mar. 6, 1985 | [JP] | Japan | 60-44185 |

[51] Int. Cl.$^5$ ............ C12P 17/02; C12P 13/00; C12N 1/12
[52] U.S. Cl. ............ 435/117; 435/123; 435/128; 435/280; 435/822; 435/252.1
[58] Field of Search ............ 435/123, 117, 280, 822, 435/170, 252.1, 128

[56] References Cited

U.S. PATENT DOCUMENTS

| 4,368,267 | 1/1983 | Hou et al. . |
| 4,956,284 | 9/1990 | Phillips ............ 435/123 |

FOREIGN PATENT DOCUMENTS

| 0193227 | 2/1986 | European Pat. Off. . |
| 0193228 | 2/1986 | European Pat. Off. . |
| 9216595 | 12/1984 | Japan . |
| 291163 | 4/1963 | Netherlands ............ 435/123 |
| 0291163 | 5/1965 | Netherlands . |
| 2028315 | 3/1980 | United Kingdom . |

OTHER PUBLICATIONS

Goodfellow et al. "The Biology of Actinomycetes" 1984, Academic Press, pp. 74–75.
Ohta et al., *Agric. Biol. Chem.* 43(10) pp. 2099–2104, 1979.

Primary Examiner—Irene Marx
Attorney, Agent, or Firm—Sughrue, Mion, Zinn, Macpeak & Seas

[57] ABSTRACT 2,3-Epoxypropyl ethers valuable as intermediates for preparing medicaments and the like are prepared from the corresponding allyl ethers by means of epoxide-producing microorganisms belonging to Nocardia, Brevibacterium, Corynebacterium, Pseudomonas, Rhodococcus, Arthrobacter or Micrococcus.

10 Claims, No Drawings

PROCESS FOR THE PREPARATION OF EPOXIDES BY MEANS OF MICROORGANISMS

This is a division of application No. 07/700,326 filed May 9, 1991; (abandoned) which is a continuation of 07/268,648 filed Nov. 8, 1988 (abandoned); which is a continuation of 06/737,966 filed May 28, 1985 (abandoned).

FIELD OF THE INVENTION

The present invention relates to a process for the preparation of epoxides by means of microorganisms, more particularly, a process for the preparation of 2,3-epoxypropyl ethers from the corresponding allyl ethers by means of microorganisms.

BACKGROUND OF THE INVENTION 2,3-Epoxypropyl phenyl ethers, a sort of 2,3-epoxypropyl ethers, are important as starting materials for medicaments, particularly, as intermediates for syntheses of β-blockers, since they can be converted into aryloxypropanolamines by ring cleavage using amines, as shown by the following reaction formula:

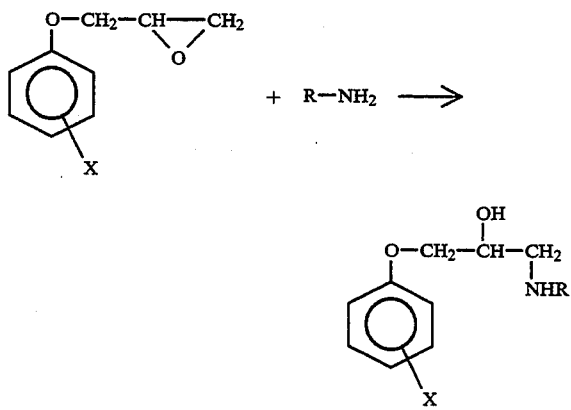

Also, 2,3-epoxypropyl naphthyl ethers are important, alike the 2,3-epoxypropyl phenyl ethers, as intermediates for syntheses of β-blockers. Further, various valuable compounds were synthesized from 2,3-epoxypropyl benzyl ethers via γ-butyrolactones.

The 2,3-epoxypropyl ethers obtainable by the process of the present invention are important as intermediates for the preparation of medicaments, agricultural chemicals and the like, since they are optically active and so various optically active derivatives can be synthesized starting from them.

Hitherto, as processes for preparing epoxides from the corresponding olefins were known chemical oxidation processes using a peroxide such as hydrogen peroxide or percarboxylic acids as an oxidizing agent, and biochemical oxidation processes using microorganisms. According to the biochemical processes using microorganisms, epoxides were prepared by treating the corresponding linear olefins or the corresponding alkenylbenzenes such as styrene, allylbenzene or the like, with microorganisms belonging to Nocardia, Pseudomonas, Brevibacterium, Corynebacterium, Mycobacterium, Arthrobacter, Acinetobacter, Alcaligenes, Methylobacterium, Methylococcus, Methylocinus, or the like.

In the epoxidation by means of microorganisms, however, the sorts of olefins which can be epoxidized were limited depending on the sort of the microorganism used. For example, it was reported that Pseudomonas oleovorans did not epoxidize propylene, 1-butene, 2-octene, cis-5-decene, cyclohexene and styrene [S. W. May, R. D. Schwartz, B. J. Abbott and O. S. Zaborsky, Biochim. Biophys. Acta., 403,245-255 (1975)], although α-olefins of $C_6$ to $C_{12}$ [B. J. Abbott and C. T. Hou, Appl. Microbiol., 26, 86-91 (1973)], α,ω-dienes [S. W. May, R. D. Schwartz, B. J. Abbott and O. S. Zaborsky, Biochim. Biophys. Acta., 403,245-255 (1975)] and allylbenzene [M-J de Smet, J. Kingma, H. Wynberg and B. Witholt, Enzyme Microb. Technol., 5,352-360 (1983)] were epoxidized.

On the other hand, Nocardia corallina epoxidized α-olefins of $C_3$ to C18 (Japanese Patent Publication No. 40/81) and also inner olefins such as 2-octene, 3-octene and the like (Japanese Patent Laid-Open No. 141791/83).

Thus, the sorts of olefins which can be epoxidized differ depending on the sort of the microorganism used, and accordingly it is necessary to examine individual olefins and individual microorganisms. As for the oxygen-containing unsaturated compounds such as allyl ethers, among compounds having a C—C double bond, any process for preparing epoxides from them by means of microorganisms is not known as yet.

Moreover, as for the preparation of optically active epoxides by means of microorganisms, any process for preparing optically active epoxides from oxygen-containing unsaturated compounds such as allyl ethers by means of microorganisms is not known as yet, although it is known that optically active epoxides are formed in the preparation of epoxides from linear olefins by microorganisms belonging to Corynebacterium or Pseudomonas and also in the preparation of epoxides from allylbenzene by microorganisms belonging to Pseudomonas.

Now, after making search for microorganisms capable of producing epoxides from allyl ethers, it has been found that epoxide-producing microorganisms belonging to Arthrobacter, Brevibacterium, Corynebacterium, Micrococcus, Nocardia, Pseudomonas or Rhodococcus produce epoxides from the corresponding allyl ethers and that the epoxides produced are optically active. Thus, the present invention has been accomplished.

That is, the object of the present invention resides in providing a novel process for the preparation of 2,3-epoxypropyl ethers valuable as intermediates for preparing medicaments and the like, by means of epoxide-producing microorganisms belonging to Arthrobacter, Brevibacterium, Corynebacterium, Micrococcus, Nocardia, Pseudomonas or Rhodococcus.

SUMMARY OF THE INVENTION

A characteristic feature of the present invention resides in producing 2,3-epoxypropyl ethers by treating the corresponding allyl ethers of the general formula $X-O-CH_2-CH=CH_2$ (I), as defined hereinafter, with microorganisms having an ability of producing epoxides which are selected from the group of microorganisms belonging to Arthrobacter, Brevibacterium, Corynebacterium, Micrococcus, Nocardia, Pseudomonas or Rhodococcus under an aerobic condition, and isolating the epoxides produced.

A further characteristic feature of the present invention resides in producing the epoxides more advantageously by effecting the treatment with the abovementioned microorganisms in the presence of a waterinsoluble organic solvent.

Examples of the starting materials and the epoxides produced therefrom according to the present invention are shown by the following schemes:

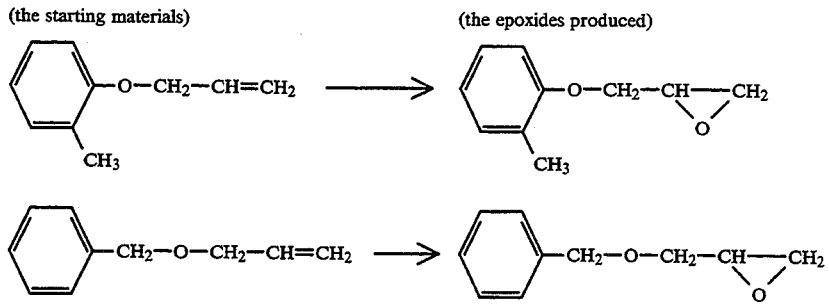

DESCRIPTION OF THE PREFERRED EMBODIMENT

As examples of the microorganisms belonging to Arthrobacter, Brevibacterium, Corynebacterium, Micrococcus, Nocardia, Pseudomonas or Rhodococcus, which are used in the present invention, there can be mentioned those strains as listed in the following Table 1. These strains are easily available, being deposited at American Type Culture Collection under the respective ATCC numbers.

TABLE 1

| | | |
|---|---|---|
| 1. | Arthrobacter roseoparaffinus | ATCC 15584 |
| 2. | Arthrobacter petroleophagus | ATCC 21494 |
| 3. | Arthrobacter rubellus | ATCC 21495 |
| 4. | Arthrobacter sp. | ATCC 27778 |
| 5. | Brevibacterium butanicum | ATCC 21196 |
| 6. | Corynebacterium fujiokense | ATCC 21496 |
| 7. | Rhodococcus Sp. | ATCC 15108 |
| 8. | Micrococcus paraffinolyticus | ATCC 15589 |
| 9. | Nocardia corallina | ATCC 31338 |
| 10. | Rhodococcus rhodochrous | ATCC 21197 |
| 11. | Rhodococcus rhodochrous | ATCC 21198 |
| 12. | Pseudomonas oleovorans | ATCC 29347 |
| 13. | Rhodococcus rhodochrous | ATCC 29675 |
| 14. | Rhodococcus rhodochrous | ATCC 29670 |
| 15. | Rhodococcus rhodochrous | ATCC 29672 |
| 16. | Rhodococcus sp. | ATCC 29673 |
| 17. | Rhodococcus sp. | ATCC 29674 |

The allyl ethers which are used in the present invention as substrates for producing epoxides by treating with the above microorganisms are those of the general formula (I)

$$X\text{—}O\text{—}CH_2\text{—}CH=CH_2 \qquad (I)$$

wherein X represents a radical selected from the group consisting of (a) phenyl and substituted phenyl radicals

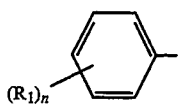

in which $R_1$ denotes either one, or two or more, selected from the group consisting of hydrogen, methyl, ethyl, n-propyl, iso-propyl, n-butyl, iso-butyl, t-butyl, methoxy, ethoxy, n-propoxy, iso-propoxy, n-butoxy, iso-butoxy, t-butoxy, halogeno, cyano, cyclopentyl, allyl, allyloxy, methoxyethyl and benzyloxy, and n is an integer of 1 to 3, said $R_1$'s being the same or different from one another when n is an integer of 2 to 3, (b) α- and β-naphthyl radicals and their substituted radicals

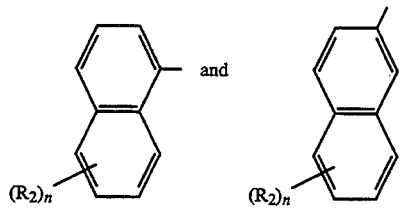

in which $R_2$ denotes either one, or two or more, selected from the group consisting of hydrogen, methyl, ethyl, n-propyl and iso-propyl, and n is an integer of 1 to 4, said $R_2$'s being the same or different from one another when n is an integer of 2 to 4, and (c) benzyl radical

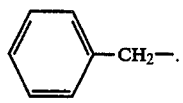

More particularly, allyl phenyl ether, α-naphthyl allyl ether, 2-methylphenyl allyl ether, 4-n-butylphenyl allyl ether, 2,5-dimethylphenyl allyl ether, 2,3-dimethylphenyl allyl ether, 2,6-di-t-butyl-4-methylphenyl allyl ether, 2-allylphenyl allyl ether, 2-cyanophenyl allyl ether, 2-cyclopentylphenyl allyl ether, 2-methoxyphenyl allyl ether, 2-chlorophenyl allyl ether, 2-allyloxyphenyl allyl ether, 4-β-methoxyethylphenyl allyl ether, 4-butoxyphenyl allyl ether, 3-methylphenyl allyl ether, 2-chloro-5-methylphenyl allyl ether, benzyl allyl ether and the like can be mentioned as examples of the allyl ethers.

According to the present invention, these allyl ethers are used as substrates, individually or as a mixture of two or more of them.

The allyl group of these allyl ethers is epoxidized by the microorganisms. Among the above-mentioned allyl ethers, allylphenyl allyl ether is epoxidized only at the allyl group bonded by ether linkage, and allyloxyphenyl allyl ether is epoxidized only at one allyl group. The epoxides produced according to the present invention are optically active.

To produce epoxides from the allyl ethers by the microorganisms belonging to Arthrobacter, Brevibacterium, Corynebacterium, Micrococcus, Nocardia, Pseudomonas and Rhodococcus, according to the present invention, (a) a method of incubating the allyl ethers under an aerobic condition with the precultivated cells of the microorganisms or (b) a method of cultivating the microorganisms under an aerobic condition in a culture medium containing the allyl ethers may be applied.

In the method (a) of incubating the allyl ethers with the precultivated cells, the microorganism is precultured under an aerobic condition in a medium consisting of assimilable carbon sources such as glucose, sucrose, molasses, starchhydrolysate, propane, butane, octane, dodecane, tetradecane, ethylene, propylene, 1-butene, 1,3-butadiene, acetic acid, ethanol, etc. , or nitrogen sources such as ammonium chloride, ammonium sulfate, ammonium phosphate, ammonium nitrate, urea, aqueous ammonia, aminoacids and other assimilable organic nitrogen compounds, inorganic salts such as potassium phosphate, sodium phosphate, magnesium sulfate, manganese sulfate, ferrous sulfate, ferric chloride, calcium chloride, manganese chloride, etc., salts of boron, copper, zinc, etc., i.e. , the so-called "trace elements", and if necessary, those substances which stimulate the growth of microorganism, such as vitamins, yeast extract, corn steep liquor, etc. To the cultured solution thus obtained, or to a suspension of the cells harvested therefrom or to immobilized cells prepared therefrom, are added the ally ethers and, if necessary, these organic solvents as described hereinafter, and then an oxygen-containing gas such as air, oxygen gas, oxygen-enriched gas, etc. is provided to cause the reaction.

The reaction is performed at a pH of 5 to 9 and a temperature of 20° to 50° C. for ½ to 6 days, as suitably prescribed depending on the microorganisms and allyl ethers used. Although the reaction is performed usually under normal pressure, it is also possible to improve the epoxide-productivity by carrying out the reaction under elevated pressure. In addition, it is possible to maintain or elevate the cell concentration and the epoxide-productivity of cells by suitably adding the carbon source, the nitrogen source and the other ingredients as used in the cell-cultivation, to the reaction mixture in the course of the reaction.

The ratio of the allyl ethers to the aqueous liquor containing cells used in the reaction is usually 0.1 to 50 vol/vol %, preferably, 0.5 to 20 vol/vol %.

The reaction can be performed by either of a batchwise process or a continuous process, or also by a semi-continuous process wherein the allyl ethers or other ingredients are supplemented continuously or intermittently in the course of the reaction.

The epoxides produced by the reaction are separated and purified by conventional methods such as phase separation, extraction, distillation and the like.

The method (b) is intended for producing epoxides by one step by adding the allyl ethers and, if necessary, those organic solvents as described hereinafter to the medium for the precultivation in the method (a). As conditions for cultivation (such as pH, temperature, pressure, amount of allyl ethers added, etc.), mode of cultivation and means of separation and purification of epoxides, the same reaction conditions, reaction mode and means for separation and purification as employed in the method (a) may be used.

As described above, the present invention encompasses or covers also an embodiment of performing the reaction of epoxidizing the allyl ethers with the microorganisms, in the presence of water-insoluble organic solvents. Therefore, such embodiment is explained hereunder.

The water-insoluble organic solvents which may be present on carrying out the epoxidation of the allyl ethers by means of the microorganisms (hereinafter, referred to merely as organic solvents) are those organic solvents selected from the group consisting of paraffins of $C_9$ to $C_{17}$, olefins of $C_{10}$ to $C_{18}$, halogenated paraffins of $C_9$ to $C_{16}$ and alkylbenzenes having one alkyl side chain of $C_6$ to $C_{15}$. These organic solvents may be used individually or as a mixture of two or more of them.

Now, more detailed explanation is given as to the organic solvents.

Among paraffins of $C_9$ to $C_{17}$, normal paraffins are those contained in kerosene and gas oil fractions of petroleum in an amount of about 20 to 25%. They are separated and recovered by means of zeolite (or molecular sieve) or the like, after hydrodesulfurization of the fraction having boiling points of about 160° to 350° C. They are generally used as materials for soft-type detergents.

The above paraffins containing a number of carbon atoms toward the high end of the range have a higher epoxidation-accelerating effect and the $C_{12}$ to $C_{16}$ paraffins are especially preferred. By the way, those containing less than 9 carbon atoms do not show any epoxidation-accelerating effect and, on the other hand, those containing more than 17 carbon atoms are of no practical use because they show only a lower epoxidation-accelerating effect and moreover they solidify at room temperature.

Further, among the above paraffins, isoparaffins are those coexisting with the normal paraffins in the above-mentioned fractions. Although they can be separated from normal paraffins by rectification, it is convenient in practice to use them in the form of mixtures with normal paraffins. They generally have side chains of short length, such as methyl, ethyl and the like. Isoparaffins of $C_{12}$ to $C_{16}$ are especially preferable for the purpose of accelerating epoxidation.

The olefins of $C_{10}$ to $C_{18}$ may be lower polymers or oligomers of propylene or butylene. Those commercially available as reagents may also be applied. Generally, they are linear or lower branched monoolefins.

By the way, olefins containing less than 10 carbon atoms do not show any epoxidation-accelerating effect and, on the other hand, those containing more than 18 carbon atoms are of no practical use because they show only a lower epoxidation-accelerating effect and moreover they are highly viscous.

The halogenated paraffins of $C_9$ to $C_{16}$ as the organic solvents are those chlorinated paraffins and brominated paraffins which include decyl chloride, undecyl chloride, undecyl bromide, dodecyl bromide, tetradecyl bromide, hexadecyl bromide, etc. Both the halogenated paraffins containing less than 9 carbon atoms and the halogenated paraffins containing more than 16 carbon atoms do not show any epoxidation-accelerating effect.

The alkylbenzenes having one alkyl side chain of $C_6$ to $C_{15}$ are those usually utilized as intermediates for hard or soft detergents, whose side chain is a linear or branched alkyl group. When the length of the side chain is outside the range of $C_6$ to $C_{15}$, any epoxidation-accelerating effect is not recognized or the epoxidation-accelerating effect is too low to be used practically.

The ratio of the above-mentioned organic solvents to the cultured broth or the suspension of the cells may vary depending on the sorts of the organic solvents used. However, it is usually 1 to 200 vol/vol %, preferably 5 to 100 vol/vol %.

The same reaction conditions, reaction mode and means for separation and purification of the epoxides formed, as described above, may be applied also in the case of performing the reaction in the presence of the organic solvents. The epoxide-productivity may be significantly elevated by the presence of the organic solvents.

The epoxides obtained according to the present invention are optically active and so they can be utilized advantageously, especially as starting materials for synthesizing physiologically active substances such as medicaments.

Hereinafter, the present invention is further explained more particularly, by giving Examples. The invention, however, shall never be limited to these Examples.

EXAMPLE 1

Preparation of cell suspension

As regards the 11 microorganisms listed in the following Table 3 except *Pseudomonas oleovorans*, a 100 ml of NBG medium (a liquid medium prepared by adding tap-water to 10 g of Lab-Lemco Powder from "Oxoid", 10 g of bacteriological peptone, 10 g of glucose and 5 g of sodium chloride to make the whole volume into 1 liter and adjusted the pH of the solution at 7.5 with 1N-aqueous sodium hydroxide solution and then autoclaved at 120° C. for 15 minutes) placed in a 500 ml shake flask was inoculated with 3 loopfuls of cells and cultivated at 30° C. for 48 hours under oscillation.

As for *Pseudomonas oleovorans* in Table 3, the microorganism was transferred from a nutrient agar slant to a nutrient agar slant supplemented with 1% of glucose and incubated at 30° C. for 24 hours. A 100 ml of a minimal salt medium of the following Table 2 and 2 ml of octane placed in a 500 ml shake flask was inoculated with 2 loopfuls of cells and cultivated at 30° C. for 16 hours under oscillation. The medium was autoclaved at 120° C. for 20 minutes. Octane was sterilized through a 0.2 μm membrane filter.

A cell suspension of each microorganism was prepared by washing the harvested cells once with 0.01M phosphate buffer (pH 7.5) and then once with the reaction medium as described hereinafter, and thereafter resuspending the cells in the same reaction medium. The concentration of cells in the cell suspension was adjusted to be within the range of 3.5 to 4.0 g/l in dry cell basis.

| Reaction medium: | $K_2HPO_4$ | 1.74 g |
|---|---|---|
| | $MgSO_4.7H_2O$ | 1.50 g |
| | $FeSO_4.7H_2O$ | 0.05 g |
| | deionized water | 1 l |

The pH was adjusted at 8.0 with $2N-H_2SO_4$.

TABLE 2

| Minimal salt medium | |
|---|---|
| $(NH_4)_2HPO_4$ | 10.0 g |
| $K_2HPO_4$ | 5.0 g |
| $Na_2SO_4$ | 0.5 g |
| $CaCl_2$ (50 g/l) | 1.0 ml |
| Salt "B" | 10.0 ml |
| $MgSO_4.7H_2O$ | 40.0 g |
| $FeSO_4.7H_2O$ | 2.0 g |
| $MnSO_4.H_2O$ | 1.6 g |
| NaCl | 2.0 g |

TABLE 2-continued

| Minimal salt medium | |
|---|---|
| distilled water | 1 l |
| Trace metal solution | 1.0 ml |
| $H_3BO_3$ | 0.50 g |
| $CuSO_4.5H_2O$ | 0.04 g |
| $Na_2MoO_4.H_2O$ | 0.20 g |
| $ZnSO_4.7H_2O$ | 8.00 g |
| $CuCl_2.6H_2O$ | 0.20 g |
| distilled water | 1 l |
| Distilled water | 1 l |

TABLE 3

| | Microorganism Used | | Amounts of the epoxide produced (mg) |
|---|---|---|---|
| 1. | *Arthrobacter roseoparaffinus* | ATCC 15584 | 0.8 |
| 2. | *Arthrobacter petroleophagus* | ATCC 21494 | 0.06 |
| 3. | *Arthrobacter rubellus* | ATCC 21495 | 0.1 |
| 4. | *Brevibacterium butanicum* | ATCC 21196 | 0.7 |
| 5. | *Corynebacterium fujiokense* | ATCC 21496 | 0.2 |
| 6. | *Pseudononas oleovorans* | ATCC 29347 | 0.02 |
| 7. | *Rhodococcus rhodochrous* | ATCC 29670 | 0.1 |
| 8. | *Rhodococcus rhodochrous* | ATCC 29672 | 0.1 |
| 9. | *Rhodococcus rhodochrous* | ATCC 19675 | 0.05 |
| 10. | *Nocardia corallina* | FERM-P-4094 ATCC 31338 | 10.3 |
| 11. | *Rodococcus rhodochrous* | ATCC 21197 | 0.5 |
| 12. | *Nocardia paraffinica* | ATCC 21198 | 0.2 |

Reaction and analysis of the product

In a 500 ml shake flask were placed 20 ml of the above cell suspension and 1 ml of allyl phenyl ether. After incubation under oscillation at 30° C. for 24 hours, the 2,3-epoxypropyl phenyl ether produced was extracted with 40 ml of ether and its amount was determined by a gas chromatograph equipped with a flame ionization detector and a glass column 2 m long packed with 3% DEGS (diethylene glycol succinate) on Uni-Dort B 80–100 mesh.

Results

The sorts of microorganisms used and the amounts of the epoxide produced by each microorganism are shown in Table 3.

EXAMPLE 2

*Nocardia corallina* ATCC 31338 (FERM-P-4094) was cultivated according to the procedure described in Example 1 and its cell suspension was prepared. The reaction was carried out in the same manner as described in Example 1, by two methods, i.e., by a reaction method (a) wherein 1 ml of each of the starting materials ethers as described in the following Table 4 was added to 20 ml of the cell suspension, and a reaction method (b) wherein 0.4 ml of each of the starting materials ethers and 2 ml of n-hexadecane were added to 20 ml of the cell suspension.

The reaction was carried out either 24 or 72 hours. The sorts of the ethers used as the starting material and the amounts of the epoxide produced from each ether are shown in Table 4. The epoxides were assayed in the same manner as described in Example 1.

TABLE 4

| Ethers used as the starting material | Reaction time (hours) | Amounts of the epoxide produced (mg) | |
| --- | --- | --- | --- |
| | | Reaction method (a) | Reaction method (b) |
| 2-methylphenyl allyl ether | 24 | 19.0 | 36.0 |
| 3-methylphenyl allyl ether | 24 | 12.7 | 25.0 |
| 4-methylphenyl allyl ether | 24 | 23.3 | 47.3 |
| 2-allylphenyl allyl ether* | 24 | 16.5 | 27.6 |
| | 72 | 20.4 | 64.9 |
| 2-allyloxypheny, allyl ether** | 24 | 27.9 | 20.5 |
| 2-chloro-5-methylphenyl allyl ether | 72 | 0.1 or less | 3.7 |
| α-naphthyl allyl ether | 72 | 0.1 or less | 4.1 |

*the product was 2-allylphenoxymethyl oxirane
**the product was a monoepoxide

EXAMPLE 3

Brevibacterium butanicum ATCC 21196 was cultivated according to the procedure described in Example 1 and its cell suspension was prepared. The reaction was carried out in the same manner as described in Example 1 by two methods, i.e., by a reaction method (a) wherein 1 ml of each of the starting materials ethers as described in the following Table 5 was added to 20 ml of the cell suspension, and a reaction method (b) wherein 0.4 ml of each of the starting materials ethers and 2 ml of n-hexadecane were added to 20 ml of the cell suspension.

The reaction was carried out for 24 hours. The sorts of the ethers used as the starting material and the amounts of the epoxide produced from each ether are shown in Table 5. The epoxides were assayed in the same manner as described in Example 1.

TABLE 5

| Ethers used as the starting material | Amounts of the epoxide produced (mg) | |
| --- | --- | --- |
| | Reaction method (a) | Reaction method (b) |
| 2-methylphenyl allyl ether | 1.5 | 3.2 |
| 3-methylphenyl allyl ether | 1.0 | 2.0 |
| 4-methylphenyl allyl ether | 1.8 | 3.5 |
| 2-allylphenyl allyl ether* | 1.3 | 2.8 |

*the product was 2-allylphenoxymethyl oxirane

EXAMPLE 4

A cell suspension of Nocardia corallina ATCC 31338 was prepared according to the procedure described in Example 1. The cell concentration was adjusted to 15 g/l in dry cell basis. 20 ml of the cell suspension, 1 ml of 2allylphenyl allyl ether as the starting material and 1 ml of each of the organic solvents described in the following Table 6 were placed in a 500 ml shake flask, and the reaction was carried out in the same manner as described in Example 1. After the reaction for 24 hours, the organic solvent layer was extracted with 40 ml of ether and the amount of the 2-allylphenoxymethyloxirane produced was determined according to the method described in Example 1. The sorts of the organic solvents used and the amounts of the epoxide produced are shown in Table 6.

TABLE 6

| Organic solvents used | Amounts of the epoxide produced (mg) |
| --- | --- |
| Paraffins | |
| n-decane | 110 |
| n-dodecane | 125 |

TABLE 6-continued

| Organic solvents used | Amounts of the epoxide produced (mg) |
| --- | --- |
| n-tridecane | 140 |
| n-tetradecane | 160 |
| n-hexadecane | 130 |
| paraffin mixture | 150 |
| Olefins | |
| 1-dodecene | 85 |
| 1-hexadecene | 115 |
| Halogenated paraffins | |
| 1-chlorododecane | 145 |
| 1-chlorotetradecane | 120 |
| Alkylbenzenes | |
| dodecylbenzene | 135 |
| tridecylbenzene | 130 |

*a mixture of 95% by weight of each normal paraffin of $C_9$ to $C_{16}$ and 5% by weight of each isoparaffin of $C_9$ to $C_{16}$ Next, for reference, the optical purities of the epoxides produced using Nocardia corallina ATCC 31338 are shown in the following Table 7.

By the way, the optical purity was determined according to the procedure of J. A. Dale, D. L. Dull and H. S. Mosher, J. Org. Chem., 34, 2453 (1963). Namely, each epoxide was reduced with LiAlH$_4$ to the corresponding 1-phenoxy-2-propanol, and then the latter was esterified with (+)-α-methoxy-α-trifluoromethylphenylacetyl chloride. By measuring NMR spectra of $^{19}F$ in the ester, the optical purity was calculated from the ratio of peak intensity of the diasteromers.

TABLE 7

| Epoxides | optical purity (% e.e.) | Absolute configuration |
| --- | --- | --- |
| phenoxymethyloxirane | 67 | S |
| (2-methylphenoxy)methyloxirane | 73 | S |
| (3-methylphenoxy)methyloxirane | 5 | S |
| (4-methylphenoxy)methyloxirane | 79 | S |
| (2-allylphenoxy)methyloxirane | 53 | S |
| (2-allyloxyphenoxy)methyloxirane | 58 | S |
| 1-naphthoxymethyloxirane | 71 | R |

EXAMPLE 5

A cell suspension of Brevibacterium butanicum ATCC was prepared according to the same procedure as described in Example 1. The cell concentration was adjusted to 7 to 8 g/l in dry basis. 20 ml of the cell suspension, L ml of 2-allylphenyl allyl ether as the starting material and 1 ml of each of the organic solvents described in the following Table 8 were placed in a 500 ml shake flask, and the reaction was carried out in the same manner as described in Example 1. After the reaction for 24 hours, the organic layer was extracted with 40 ml of ether and the amount of 2-allylphenoxymethyloxirane produced was determined according to the method described in Example 1. The sorts of the organic solvents used and the amounts of the epoxide formed are shown in Table 8.

TABLE 8

| Organic solvents used | Amounts of the epoxide produced (mg) |
| --- | --- |
| Paraffins | |
| n-decane | 4.5 |
| n-dodecane | 5.1 |
| n-tridecane | 5.7 |
| n-tetradecane | 6.6 |
| paraffin mixture* | 6.1 |

TABLE 8-continued

| Organic solvents used | Amounts of the epoxide produced (mg) |
| --- | --- |
| Olefins | |
| 1-dodecene | 3.5 |
| 1-hexadecene | 4.7 |
| Halogenated paraffins | |
| 1-chlorododecane | 6.0 |
| 1-chlorotetradecane | 4.9 |
| Alkylbenzenes | |
| dodecylbenzene | 5.5 |
| tridecylbenzene | 5.3 |
| Referential Example | |
| no organic solvent | 2.5 |

*a mixture of 95% by weight of each normal paraffin of $C_9$ to $C_{16}$ and 5% by weight of each isoparaffin of $C_9$ to $C_{16}$

EXAMPLE 6

20 ml of a synthetic medium (a liquid medium prepared by adding ion-exchanged water to 4 g of $(NH_4)_2HPO_4$, 2.5 g of $Na_2HPO_4.12H_2O$, 2 g of $KH_2PO_4$, 0.5 g of $MgSO_4.7H_2O$, 30 mg of $FeSO_4.7H_2O$, 60 mg of $CaCl_2.2H_2O$ and 200 mg of yeast extract from "Difco" to make the whole volume into 1 l and then autoclaved at 120° C. for 15 minutes) placed in a 500 ml shake flask was inoculated with 2 loopfuls of each of the 6 microorganisms listed on the following Table 9. The flask was stopperred and 120 ml of propane was introduced into the flask. The flask was incubated at 30° C. for 120 hours lander oscillation. A cell suspension of each of the 6 microorganisms was prepared according to the method described in Example 1.

5 ml of the above cell suspension and 250 μl of phenyl ally ether were placed in a test tube having an outer diameter of 24 mm, and the test tube was stopperred. After the incubation at 30° C. for 24 hours under oscillation, the organic layer was extracted with 20 ml of ether and the amount of 2,3-epoxypropyl phenyl ether produced was determined according to the method described in Example 1.

The results are shown in Table 9.

TABLE 9

| Microorganism used | | Cell concentrations (mg/l) | Amounts of the epoxide produced (mg) |
| --- | --- | --- | --- |
| Arthrobacter petroleophagus | ATCC 21494 | 0.28 | 0.23 |
| Arthrobacter sp. | ATCC 27778 | 1.2 | 0.04 |
| Rhodococcus rhodochrous | ATCC 29670 | 4.0 | 0.05 |
| Rhodococcus rhodochrous | ATCC 29672 | 4.0 | 0.04 |
| Rhodococcus sp. | ATCC 29673 | 1.12 | 0.05 |
| Rhodococcus sp. | ATCC 29674 | 1.6 | 0.08 |

Ether was removed from the solution in ether of the product obtained by the reaction using *Arthrobacter rubellus* ATCC 21495 as described in Example 1. The residue was dissolved in a mixture of 4 ml of isopropanol and 2 ml of isopropylamine and heated at 80° C. for 4 hours in a 20 ml Pyrex ample. Then, the reaction mixture was evaporated to dryness. Thereafter, the residue was dissolved in 10 ml of benzene and the organic layer was extracted twice with 20 ml of 1N—HCl. To the aqueous layer was added 20 ml of 6N—NaOH and then the resulting mixture was extracted with 20 ml of benzene. The benzene layer was dried over $Na_2SO_4$, and evaporated to dryness. The residue was transferred into a 7 ml vial and then, derivatized with 100 μl of bis(trimethylsilyl)trifluoro-acetamide under heating at 60° C. for 15 minutes. Then, 100 μl of 1M solution of N-heptafluorobutyryl-L-prolylchloride in dichloromethane was added to the reaction mixture. One μl of the final solution was injected into a gaschromatograph equipped with a flame ionization detector and a 60 m long glass capillary column coated with OV225.

The ratio of the peak areas of the two diastereomers was 74.5 (the peak of shorter retention time) vs. 25.5 (the peak of longer retention time) The optical purity of the 2,3-epoxypropyl phenyl ether produced by *Arthrobacter rubellus* ATCC 21495 was calculated to be 49% e.e.

EXAMPLE 8

According to the same procedure as described in Example 1, cell suspensions of the 9 microorganisms described in the following Table 10 were prepared. The cell concentration of each cell suspension was adjusted to be within the range of 3.5 to 4.0 g/l in dry cell basis.

Reaction and analysis of the product

Twenty ml of the above cell suspension, 400 μl of allyl benzyl ether and 8 ml of n-hexadecane were placed in a 500 ml shake flask. After incubation under oscillation at 30° C. for 24 hours, the 2,3-epoxypropyl benzyl ether produced was extracted with 40 ml of ether and its amount was determined according to the method described in Example 1.

Results

The sorts of microorganisms used and the amounts of the epoxide produced by each microorganism are shown in Table 10.

TABLE 10

| Microorganism used | | Amounts of the epoxide produced (mg) |
| --- | --- | --- |
| *Micrococcus paraffinolyticus* | ATCC 15589 | 0.12 |
| *Arthrobacter petroleophagus* | ATCC 21494 | 0.66 |
| *Arthrobacter roseoparaffinus* | ATCC 15584 | 0.07 |
| Arthrobacter sp. | ATCC 27778 | 0.09 |
| *Rhodococcus rhodochrous* | ATCC 29675 | 0.13 |
| *Rhodococcus rhodochrous* | ATCC 21197 | 0.45 |
| Nocardia corallina | ATCC 31338 | 32.3 |
| Rhodococcus Sp. | ATCC 15108 | 0.28 |
| *Brevibacterium butanicum* | ATCC 21196 | 0.64 |

EXAMPLE 9

Using *Nocardia corallina* ATCC 31338, a cell suspension was prepared by the same procedure as described in Example 1. Five ml of the cell suspension was placed in a test tube having an outer diameter of 24 mm, and the reaction was carried out at 30° C. for 24 hours under oscillation according to four kinds of methods, i.e., a reaction method (a) wherein 100 μl of allyl benzyl ether was added to the cell suspension, a reaction method (b) wherein 100 μl of allyl benzyl ether and 5 ml of n-hexadecane were added to the cell suspension, a reaction method (c) wherein 250 μl of allyl benzyl ether was added to the cell suspension and a reaction method (d) wherein 250 μl of allyl benzyl ether and 5 ml of n-hexadecane were added to the cell suspension. The analysis was made according to the same method as described in Example 1. The amount of the phenylmethoxymethyloxirane produced in each case is shown in the following Table 11.

TABLE 11

| Methods | Amounts of the epoxide produced (mg) |
|---|---|
| (a) | 2.5 |
| (b) | 11.9 |
| (c) | 4.0 |
| (d) | 13.6 |

EXAMPLE 10

A cell suspension of *Nocardia corallina* ATCC 31338 was prepared according to the procedure described in Example 1. Five ml of the cell suspension was placed in a test tube having an outer diameter of 24 min. Then, 100 μl of ally benzyl ether and 5 ml of each of the organic solvents described in the following Table 12 were added to the cell suspension, and the reaction was carried out in the same manner as described in Example 1. After the reaction for 24 hours, the analysis of the product was made according to the same method as described in Example 1.

The amounts of the epoxide produced are shown in Table 12.

TABLE 12

| Organic solvents used | Amounts of the epoxide produced (mg) |
|---|---|
| Paraffins | |
| n-decane | 10.5 |
| n-dodecane | 13.8 |
| n-tridecane | 13.9 |
| n-tetradecane | 13.5 |
| paraffin mixture* | 12.2 |
| Olefins | |
| 1-dodecene | 12.5 |
| 1-hexadecene | 13.4 |
| Halogenated paraffins | |
| 1-chlorododecane | 11.6 |
| 1-chlorotetradecane | 12.5 |
| Alkylbenzenes | |
| dodecylbenzene | 10.8 |
| tridecylbenzene | 11.2 |

*a mixture of 95% by weight of each normal paraffin of $C_9$ to $C_{16}$ and 5% by weight of each isoparaffin of $C_9$ to $C_{16}$

EXAMPLE 11

20 ml of a synthetic medium ( a liquid medium prepared by adding ion-exchanged water to 4 g of $(NH_4)_2HPO_4$, 2.5 g of $Na_2HPO_4.12H_2O$, 2 g of $KH_2PO_4$, 0.5 g of $MgSO_4.7H_2O$, 30 mg of $FeSO_4.7H_2O$, 600 mg of $CaCl_2.2H_2O$ and 200 mg of yeast extract from "Difco" to make the whole volume into 1 l and then autoclaved at 120° C. for 15 minutes) placed in a 500 ml shake flask was inoculated with 2 loopfuls of *Nocardia corallina* ATCC 31338, and the flask was stopperred. Then, 120 ml of propylene was introduced into the flask and the flask was incubated at 30° C. for 96 hours under oscillation. The cells were washed according to the manner described in Example 1, to prepare a cell suspension.

Five ml of the above cell suspension, 250 μl of allyl benzyl ether and 5 ml of n-hexadecane were placed in a test tube having an outer diameter of 24 mm. The reaction was carried out in the manner described in Example 2, whereby 6.6 mg of phenylmethoxymethyloxirane was obtained.

EXAMPLE 12

From the ether solution of each of the nine sorts of reaction products described in Example 8, ether was removed. The residue was dissolved in a mixture of 4 ml of isopropanol and 2 ml of isopropylamine and heated at 80° C. for 4 hours in a 20 ml Pyrex ample. Then, the reaction mixture was evaporated to dryness. Thereafter, the residue was dissolved in 10 ml of benzene and the organic layer was extracted twice with 20 ml of 1N-HCl. To the aqueous layer was added 20 ml of 6N-NaOH and then the resulting mixture was extracted with 20 ml of benzene. The benzene layer was dried over $Na_2SO_4$, and evaporated to dryness. The residue was transferred into a 7 ml vial and then, derivatized with 100 μl of bis(trimethylsilyl)trifluoro-acetamide under heating at 60° C. for 15 minutes. Then, 100 μl of 1M solution of N-heptafluorobutyryl-L-prolylchloride in dichloromethane was added to the reaction mixture. One μl of the final solution was injected into a gas-chromatograph equipped with a flame ionization detector and a 60 m long glass capillary column coated with OV225. The absolute configuration and optical purity of the phenylmethoxymethyloxirane produced by each of the nine microorganisms are shown in the following Table 13.

TABLE 13

| Microorganism used | | Absolute configuration of the epoxide | Optical purity of the epoxide (% e.e.) |
|---|---|---|---|
| *Micrococcus paraffinolyticus* | ATCC 15589 | S | 27 |
| *Arthrobacter petroleophagus* | ATCC 21494 | S | 25 |
| *Arthrobacter roseoparaffinus* | ATCC 15584 | S | 22 |
| Arthrobacter sp. | ATCC 27778 | R | 46 |
| *Rhodococcus rhodochrous* | ATCC 29675 | R | 5 |
| *Rhodococcus rhodochrous* | ATCC 21197 | R | 32 |
| *Nocardia corallina* | ATCC 31338 | S | 10 |
| Rhodococcus Sp. | ATCC 15108 | S | 21 |
| *Brevibacterium butanicum* | ATCC 21196 | S | 26 |

While the invention has been described in detail and with reference to specific embodiments thereof, it will be apparent to one skilled in the art that various chances and modifications can be made therein without departing from the spirit and scope thereof.

What is claimed is:

1. A process for the preparation of epoxides comprising:
   (a) reacting an ether with a microorganism under aerobic conditions in an aqueous medium to produce the corresponding 2,3-epoxypropyl ether, and
   (b) isolating the epoxide, wherein said ether is an allyl phenyl ether and said microorganism is selected from the group consisting of *Arthrobacter roseoparaffinus* ATCC 15584, *Arthrobacter petroleophagus* ATCC 21494, *Arthrobacter rubellus* ATCC 21495, Arthrobacter sp. ATCC 27778, *Brevibacterium butanicum* ATCC 21196, *Corynebacterium fujiokense* ATCC 21496, *Pseudomonas oleovorans* ATCC 29347, *Rhodococcus rhodochrous* ATCC 29675, *Rhodococcus rhodochrous* ATCC 29670, *Rhodococcus rhodochrous* ATCC 29672, Rhodococcus sp. ATCC 29673 and Rhodococcus sp. ATCC 29674;

wherein said ether is an allyl benzyl ether and said microorganism is selected from the group consisting of *Arthrobacter roseoparaffinus* ATCC 15584, *Arthrobacter petroleophagus* ATCC 21494, Arthrobacter sp. ATCC 27778, *Brevibacterium butanicum* ATCC 21196, *Corynebacterium fujiokense* ATCC 21496 and *Rhodococcus rhodochrous* ATCC 29675; or wherein said ether is selected from the group consisting of 2-methylphenyl allyl ether, 3-methylphenyl allyl ether, 4-methylphenyl allyl ether, 2-ethylphenyl allyl ether, 2-(n-propyl)phenyl allyl ether and 2-allylphenyl allyl ether and said microorganism is *Brevibacterium butanicum* ATCC 21196.

2. The process for the preparation of epoxides as claimed in claim 1, wherein an allyl benzyl ether is reacted with a microorganism selected from the group consisting of *Arthrobacter roseoparaffinus* ATCC 15584, *Arthrobacter petroleophagus* ATCC 21494, Arthrobacter sp. ATCC 27778, *Brevibacterium butanicum* ATCC 21196, and *Corynebacterium fujiokense* ATCC 21496, and the 2,3-epoxypropyl ether produced is optically active.

3. A process for the preparation of epoxides as claimed in claim 1, wherein the reacting step occurs at a temperature of 20° to 50° C. and a pH of 5 to 9 under aerobic conditions.

4. A process for the preparation of epoxides comprising:
  (a) reacting an ether selected from the group consisting of 2-methylphenyl allyl ether, 3-methylphenyl allyl ether, 4-methylphenyl allyl ether, 2-ethylphenyl allyl ether, 2-(n-propyl)phenyl allyl ether and 2-allylphenyl allyl ether with *Brevibacterium butanicum* ATCC 21196 under aerobic conditions in an aqueous medium containing a water-insoluble organic solvent to produce the corresponding 2,3 epoxypropyl ether, and
  (2) isolating the epoxide.

5. A process for the preparation of epoxides as claimed in claim 4, wherein the water-insoluble organic solvent is selected from the group consisting of paraffinic hydrocarbons of $C_9$ to $C_{17}$, olefinic hydrocarbons of $_{10}$ to $C_{18}$, halogenated paraffins of $C_9$ to $C_{16}$, alkylbenzenes having one alkyl side chain of $C_6$ to $C_{15}$, and mixtures thereof.

6. A process for the preparation of epoxides as claimed in claim 4, wherein the water-insoluble organic solvent is present in an amount of 1 to 200 parts by volume per 100 parts by volume of said medium.

7. A process for the preparation of epoxides as claimed in claim 6, wherein the water-insoluble organic solvent is present in an amount of 5 to 100 parts by volume per 100 parts by volume of said medium.

8. A process for the preparation of epoxides as claimed in claim 4, wherein the reacting step occurs at a temperature of 20° to 50° C. and a pH of 5 to 9 under aerobic conditions.

9. A process for the preparation of epoxides as claimed in claim 5, wherein the water-insoluble organic solvent is a paraffinic hydrocarbon of $C_{12}$ to $C_{16}$.

10. A process for the preparation of epoxides as claimed in claim 9, wherein the paraffinic hydrocarbon of $C_{12}$ to $C_{16}$ is an isoparaffinic hydrocarbon of $C_{12}$ to $C_{16}$.

* * * * *